United States Patent
Trieu et al.

(10) Patent No.: US 9,220,553 B2
(45) Date of Patent: Dec. 29, 2015

(54) SYSTEM AND METHOD FOR PRESSURE MIXING BONE FILLING MATERIAL

(71) Applicant: Warsaw Orthopedic, Inc., Warsaw, IN (US)

(72) Inventors: Hai H. Trieu, Cordova, TN (US); Aashiish Agnihotri, Memphis, TN (US); Joseph Saladino, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/474,652

(22) Filed: Sep. 2, 2014

(65) Prior Publication Data

US 2014/0371753 A1 Dec. 18, 2014

Related U.S. Application Data

(62) Division of application No. 11/622,558, filed on Jan. 12, 2007, now Pat. No. 8,840,618.

(51) Int. Cl.
| | | |
|---|---|---|
| *A61B 17/88* | (2006.01) | |
| *A61B 17/70* | (2006.01) | |
| *A61F 2/44* | (2006.01) | |
| *A61L 27/56* | (2006.01) | |
| *B01F 13/06* | (2006.01) | |
| *A61B 17/56* | (2006.01) | |
| *A61F 2/30* | (2006.01) | |

(52) U.S. Cl.
CPC .............. *A61B 17/8805* (2013.01); *A61B 17/70* (2013.01); *A61B 17/8833* (2013.01); *A61F 2/4455* (2013.01); *A61L 27/56* (2013.01); *B01F 13/065* (2013.01); *A61B 2017/564* (2013.01); *A61F 2002/3092* (2013.01); *A61F 2310/00353* (2013.01); *A61L 2400/06* (2013.01); *A61L 2430/38* (2013.01)

(58) Field of Classification Search
CPC .... A61B 17/70; A61B 17/88; A61B 17/8805; A61F 2/4455; A61L 27/56
USPC ........ 606/92–94; 604/211, 224, 235; 222/390
See application file for complete search history.

(56) References Cited

U.S. PATENT DOCUMENTS

| | | | |
|---|---|---|---|
| 5,047,031 A | | 9/1991 | Constantz |
| 5,116,315 A | * | 5/1992 | Capozzi et al. ............... 604/82 |
| 5,525,148 A | | 6/1996 | Chow et al. |
| 5,650,108 A | | 7/1997 | Nies et al. |

(Continued)

OTHER PUBLICATIONS

U.S. Appl. No. 11/622,570, filed Jan. 12, 2007 in the name of Trieu, et al.

(Continued)

*Primary Examiner* — Christopher Beccia
(74) *Attorney, Agent, or Firm* — Sorell Lenna & Schmidt LLP

(57) ABSTRACT

A method for treating a vertebral bone comprises providing a bone filling material and mixing the bone filling material in a vessel to form a bone augmentation material. The method further comprises pressurizing the vessel with a pressurization source to retain a plurality of voids within the bone augmentation material. The method further includes inserting a material delivery device into the vertebral bone and injecting the bone augmentation material with the retained plurality of voids from the material delivery device and into the vertebral bone.

20 Claims, 3 Drawing Sheets

(56) References Cited

U.S. PATENT DOCUMENTS

| | | | |
|---|---|---|---|
| 5,795,922 | A | 8/1998 | Demian et al. |
| 5,820,632 | A | 10/1998 | Constantz et al. |
| 6,083,264 | A | 7/2000 | Wood et al. |
| 6,479,565 | B1 | 11/2002 | Stanley |
| 6,547,866 | B1 * | 4/2003 | Edwards et al. ............... 106/35 |
| 2005/0197422 | A1 | 9/2005 | Mayadunne et al. |
| 2006/0095138 | A1 | 5/2006 | Truckai et al. |
| 2006/0122614 | A1 | 6/2006 | Truckai et al. |
| 2006/0122625 | A1 * | 6/2006 | Truckai et al. ............... 606/94 |
| 2007/0027230 | A1 * | 2/2007 | Beyar et al. ............... 523/117 |
| 2008/0028992 | A1 * | 2/2008 | Lee et al. ............... 106/690 |

OTHER PUBLICATIONS

U.S. Appl. No. 11/622,547, filed Jan. 12, 2007 in the name of Trieu, et al.

A. Boger, S. Verrier, M. Bohner, P. Heini, E. Schneider; Properties of an injectable low modulus PMMA bone cement for vertebroplasty; European Cells and Materials vol. 10. Suppl. 1, 2005 (p. 17); AO Research Institute, Davos, Switzerland.

A. Boger, P. Heini, M. Bohner, E. Schneider; Vertebral Cancellous Bone Augmented with Stiffness-adapted PMMA Cement does not Show Acute Failure under Dynamic Loading; European Cells and Materials vol. 11. Suppl. 1, 2006 (p. 29); AO Research Institute, Davos, Switzerland.

* cited by examiner

SYSTEM AND METHOD FOR PRESSURE MIXING BONE FILLING MATERIAL

CROSS REFERENCE

This application is a divisional application of U.S. patent application Ser. No. 11/622,558 filed on Jan. 12, 2007. The related applications, incorporated by reference herein, are:

U.S. Utility patent application Ser. No. 11/622,570, filed on Jan. 12, 2007 and entitled "System and Method For Forming Porous Bone Filling Material" and U.S. Utility patent application Ser. No. 11/622,547, filed on Jan. 12, 2007 and entitled "System and Method For Forming Bone Filling Materials With Microparticles".

BACKGROUND

Bone cements and other bone filling materials are currently used throughout the skeletal system to augment or replace bone weakened or lost to disease or injury. One example of a treatment that includes the administration of bone filling material is vertebroplasty. During vertebroplasty, the cancellous bone of a vertebral body is supplemented with bone filling material. Frequently, the available bone filling materials do not possess material properties similar to the native bone. Materials, systems, and methods are needed to form and deliver bone filling materials that may be selectively matched to the natural bone undergoing treatment.

SUMMARY

In one embodiment, a method for treating a vertebral bone comprises providing a bone filling material and mixing the bone filling material in a vessel to form a bone augmentation material. The method further comprises pressurizing the vessel with a pressurization source to retain a plurality of voids within the bone augmentation material. The method further includes inserting a material delivery device into the vertebral bone and injecting the bone augmentation material with the retained plurality of voids from the material delivery device and into the vertebral bone.

In another embodiment, a bone augmentation system comprises a mixing vessel at least partially filled with a bone filling material, the mixing vessel comprising a mixing element. Mixing the bone filling material with the mixing element creates a void filled bone augmentation material. A pressurization source is connected to the mixing vessel and adapted to prevent at least some voids in the void filled bone augmentation material from escaping. A dispensing instrument comprises a dispensing reservoir and is adapted to receive the void filled bone augmentation material. The dispensing instrument further comprises a cannulated member adapted to deliver the void filled bone augmentation material into a body region adjacent cancellous bone.

In another embodiment, a method of augmenting a bone comprises mixing a bone filling material in a mixing vessel to generate a bone augmentation material comprising a plurality of voids, elevating the pressure in the mixing vessel above atmospheric pressure, retaining at least a portion of the plurality of voids within the bone augmentation material, injecting the bone augmentation material into the bone, and allowing the bone augmentation material to set to a hardened and porous condition within the bone.

Additional embodiments are included in the attached drawings and the description provided below.

DETAILED DESCRIPTION

Figure 1:
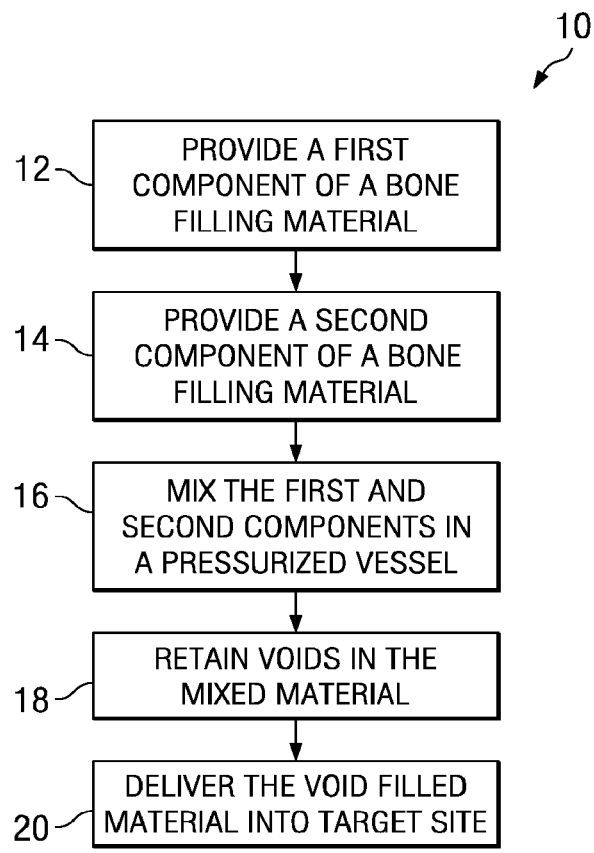
FIG. 1 is a flowchart for a process of forming a modulated bone augmentation material according to one embodiment of the disclosure.

The present disclosure relates generally to devices, methods and apparatus for augmenting bone, and more particularly, to methods and instruments for augmenting bone with a porous material. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
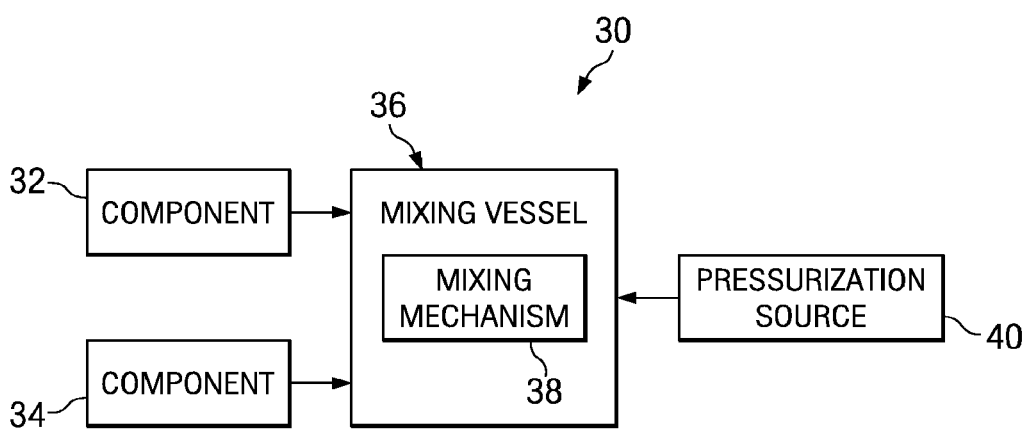
FIG. 2 is a schematic diagram of a material preparation system according to one embodiment of the present disclosure.

Referring first to FIG. 1, the reference numeral 10 refers to a method for forming a modified or modulated bone augmentation material that may better correspond to the material properties, including the modulus of elasticity, of a target bone region as compared to unmodulated bone filling material such as bone cement. At steps 12 and 14 first and second components of a bone filling material may be selected. As shown in FIG. 2, a material preparation system 30 may receive a first component of a bone filling material 32 and a second component of bone filling material 34. This embodiment describes the use of a two component bone filling material such as polymethylmethacrylate (PMMA), which is formed from a PMMA powder and a PMMA monomer. It is understood that in alternative embodiments, suitable bone filling material may be single component materials or have more than two components. In addition to PMMA bone cement, suitable bone filling materials may include calcium phosphate bone cement, calcium sulfate compounds, calcium aluminate compounds, aluminum silicate compounds, hydroxyapatite compounds, in situ curable ceramics or polymers, or other flowable materials that become more rigid after delivery. Generally, before it is modified, the bone filling material in a hardened state may have a higher modulus of elasticity than the target bone region.

Referring again to FIGS. 1 and 2, at step 16, the first component 32 and the second component 34 may be deposited in a mixing vessel 36 which comprises a mixing mechanism 38. The mixing vessel 36 may be sealable. The mixing mechanism 38 may be activated to mix the components 32, 34. Suitable mixing mechanisms may include an agitator having a rotary mixing blade, an aerator, static mixing elements or any other device operable to mix a bone filling material. Electric, manual, and pneumatic mixing mechanisms may be suitable for mixing the bone filling material. It is understood that although the mixing mechanism 38 is depicted as located within the mixing vessel 36, all or parts of the mixing mechanism may be located outside of the mixing vessel, but still provide a mixing action to the contents of the mixing vessel. An aerator or a magnetic mixing device may be examples of mixing mechanisms located outside of the mixing vessel.

As the components 32, 34 of the bone filling material are mixed, gaseous voids, such as air bubbles, may form from, for example, the mixing action of the mixing mechanism 38 and/or the chemical reaction of the first and second components 32, 34. The gaseous voids may become dispersed throughout the mixture of bone filling materials 32, 34 to form a porous modulated bone augmentation material. It is understood that the gaseous voids may contain air or other gaseous substances.

At step 18, to prevent the gaseous voids from rising through and escaping from the bone augmentation material, the contents of the mixing vessel 36 may be pressurized by a pressurization source 40 connected to the mixing vessel 36. The pressurization source 40 may raise and maintain the pressure in the mixing vessel at a level greater than atmospheric pressure. In one embodiment, the pressurization source is a pump that pumps outside air or other gaseous substances into the otherwise sealed mixing vessel. In another embodiment, the pressurization source is a container of compressed gas, such as a cartridge of compressed carbon dioxide, nitrogen, or oxygen. Other pressurization sources connectable to or integral with the mixing vessel may also be suitable.

The speed and type of the mixing mechanism 38, the shape of the mixing mechanism and mixing vessel 36, the amount of pressure provided by the pressurization source 40, and the duration of the mixing are among the factors that may contribute to the size and density of the void formation in the fluid modulated bone augmentation material, and ultimately the size and density of the pores that are formed in the hardened modulated bone augmentation material. Larger pores may impart a lower modulus than the same quantity of smaller pores. A higher density of pores may impart a lower modulus to the bone filling material than would a less dense array of pores of the same size and material properties.

The pressurization source 40 may be adjustable to control the size and density of the formed voids. For example, pressurization may be gradually reduced during the mixing process as the increasing viscosity of the bone filling material traps a greater quantity of voids. A pressure gauge may be used to monitor the pressurization and to control the adjustment of the pressurization source 40.

The mixing and pressurization may continue until the concentration of bubbles in the liquid bone augmentation material is sufficient to lower the overall modulus of elasticity of the final cured or hardened modulated bone augmentation material to a level that more closely matches the modulus of the target bone region or that at least may reduce the risk of damage to the adjacent bone that could otherwise be caused by the unmodulated bone cement. In certain patients, it may be desirable to reduce the modulus of elasticity to a level lower than natural cancellous bone. For example, a modulus of elasticity for hardened bone augmentation material that is less than five times that of cancellous bone may be suitable for some patients.

The desired size and density of the pores may be dependent upon the size of the target bone region and characteristics of the patient including the age, bone density, body mass index, or health of the patient. For example, an elderly osteoporotic vertebroplasty patient may require a more reduced modulus bone augmentation material than would a young healthy trauma victim undergoing a similar procedure. The size of the pores may be selected based upon the patient and controlled by pressurization. For example, 90% of the pores may be in the range of 1 to 2000 microns in diameter. Other suitable pore sizes may range from 10 to 1000 microns.

Other additives may be added to the bone filling material during the preparation of the bone filling material or during the pressurized mixing. Additives that include radiocontrast media may be added to the bone filling material to aid in visualizing the bone augmentation material with imaging equipment. Suitable radiocontrast materials may include barium sulfate, tungsten, tantalum, or titanium. Additives that include osteoconductive or osteoinductive materials may be added to promote bone growth into the hardened bone augmentation material. Suitable osteoconductive materials may include hydroxyapatite (HA), tricalcium phosphate (TCP), HA-TCP, calcium phosphate, calcium sulfate, calcium carbonate, and/or bioactive glasses. Suitable osteoinductive materials may include proteins from transforming growth factor (TGF) beta superfamily, or bone-morphogenic proteins, such as BMP2 or BMP7. Pharmacological agents may be added to promote healing and prevent or fight infection. Suitable pharmacological additives may include antibiotics, anti-inflammatory drugs, or analgesics.

Referring again to FIG. 1, at step 20, the modulated bone augmentation material, including any additives, may be delivered into a target bone region in a patient's anatomy. The modulated bone augmentation material may be transferred to a delivery system, such as a syringe or a threaded material dispensing system prior to delivery into the target bone region. In alternative embodiments, the bone filling material may be mixed and pressurized in the same container that will be used to dispense the mixture such that a material transfer becomes unnecessary.

Although the target bone region will often be in a bone, other bone regions, such as joints, may receive the modulated bone augmentation material to, for example, promote fusion. Examples of target bone regions may be fractured cortical or cancellous bone, osteoporotic cancellous bone, or degenerated intervertebral discs. By matching the modulated bone augmentation material to the material properties of the adjacent bone, complications associated with unaltered, high modulus bone cements may be minimized. In particular, matching the material properties may provide a uniform stress distribution, minimizing significant stress concentrations that may pose a fracture risk to adjacent bone.

Figure 3:
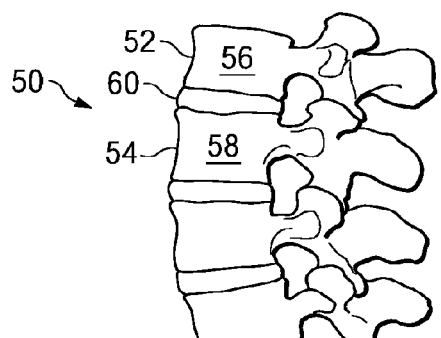
FIG. 3 is a sagittal view of a section of a vertebral column.

Referring now to FIG. 3, in one embodiment, a modulated bone augmentation material formed by method 10 may be used to augment or replace portions of a vertebral column. The reference numeral 50 refers to a healthy vertebral joint section of a vertebral column. The joint section 50 includes adjacent vertebrae 52, 54 having vertebral bodies 56, 58, respectively. An intervertebral disc 60 extends between the vertebral bodies 56, 58. Although FIG. 3 generally depicts a lumbar region of the spine, it is understood that the systems, materials, and methods of this disclosure may be used in other regions of the vertebral column including the thoracic or cervical regions.

Figure 4:
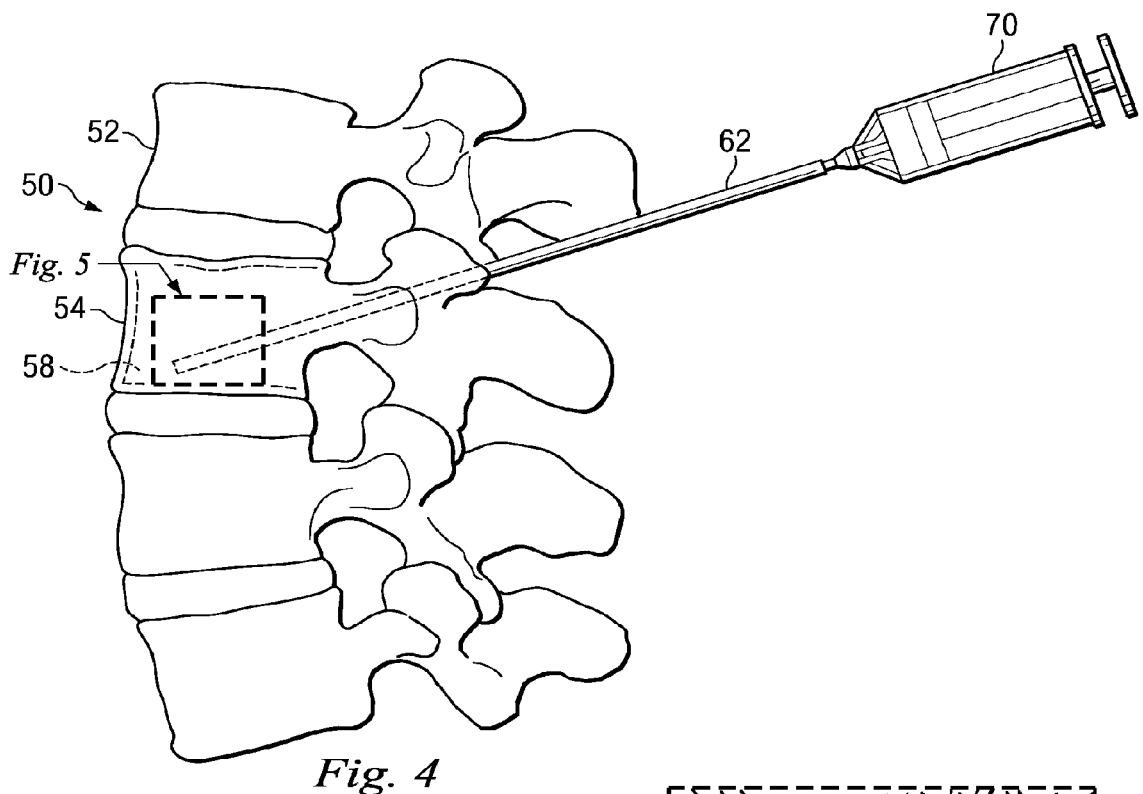
FIG. 4 is a sagittal view of a section of a vertebral column undergoing a vertebroplasty procedure using a porous bone augmentation material.
Figure 5:
FIGS. 5-6 are detailed views of the procedure of FIG. 4.
Figure 6:
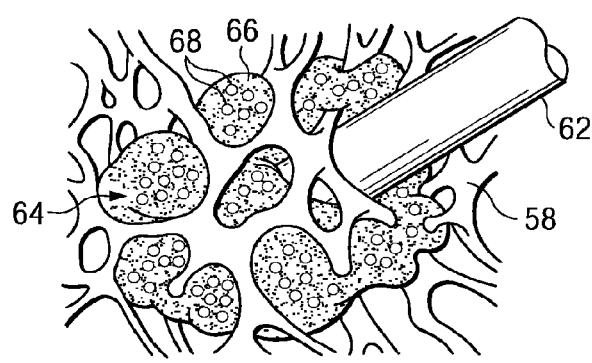
Figure 7:
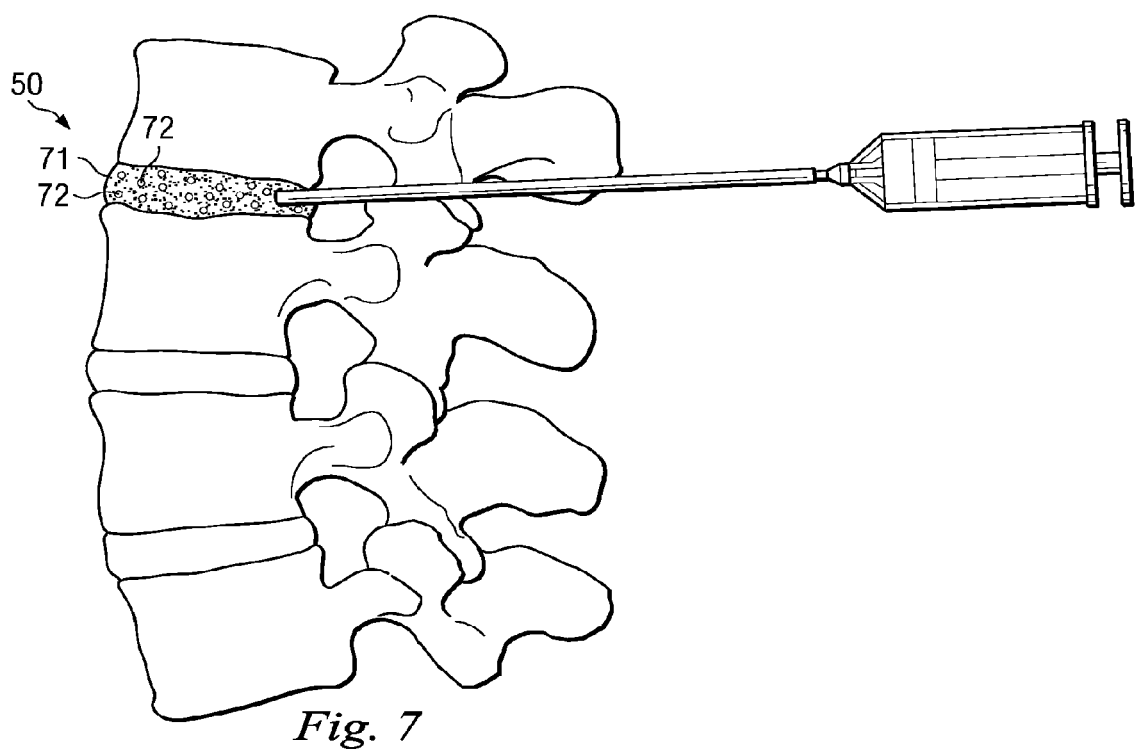
FIG. 7 is a sagittal view of a section of a vertebral column with an intervertebral disc treated with porous bone filling material.

Referring now to FIGS. 4-6, due to traumatic injury, cancer, osteoporosis or other afflictions, the vertebral body portion 58 of the vertebra 54 may begin to collapse, causing pain and loss of bone height. One procedure for restoring the vertebral height, reducing pain, and/or building mass is known as vertebroplasty. In a vertebroplasty procedure according to one embodiment of this disclosure, a stylet or other sharpened instrument (not shown) may be inserted into an injection instrument such as a cannula 62 and arranged so that a sharpened tip protrudes through the end of the cannula.

The assembled stylet and cannula 62 may then be inserted through a pedicle of the vertebra 54 and into the cancellous bone of the vertebral body 58. This insertion may be guided through the use of fluoroscopy or other imaging modalities. With the cannula 62 in place in the vertebral body 58, the stylet may be withdrawn leaving the cannula in place to serve as a pathway for delivering instruments or materials into the bone. In alternative embodiments, a surgical needle having a cannulated body and a pointed tip may be used to access the vertebral body.

Following the method 10, described above, a modulated bone augmentation material 64 comprised of bone cement 66 and gaseous voids 68 may be formed and transferred to a delivery system 70. The delivery system 70 may be a conventional syringe, having a material reservoir and a plunger mechanism movable therethrough, or a more sophisticated threaded injection system such as the type covered by, for example, U.S. Pat. No. 6,348,055 which is incorporated by reference herein. Other types of material delivery systems may also be suitable. The delivery system 70 may be actuated, such as by moving the plunger mechanism into the material reservoir, to move the bone augmentation material 64 through the cannula 62 and into the vertebra 54 where the mixture may flow into the interstices of the cancellous bone of the vertebral body 58 as shown in FIG. 6. It is understood that the gaseous voids 68 shown in FIG. 6 are not necessarily to scale but rather are merely exemplary of the random disbursement of the gaseous voids which will later form pores within the hardened bone augmentation material. As described above, within any given mixture of modulated bone augmentation material, the pores may have different sizes and/or properties. Further, the density of pores may be determined based upon the amount the original bone filling material must be modified to achieve an acceptable modulated bone augmentation material.

With the gaseous voids 68 distributed throughout the bone cement 66, the modulated bone augmentation material 64 may be cured or otherwise allowed to harden within the vertebral body 58. The gaseous voids 68 may remain suspended in the hardened bone cement 66, forming pores which reduce the overall stiffness of the modulated bone augmentation material 64. The modulus of elasticity of the hardened modulated bone augmentation material 64 may be lower than that of the unmodulated hardened bone filling material 66, alone, and closer to the modulus of elasticity of the cancellous bone of the vertebral body 58 than that of the hardened bone filling material alone. Thus, the material 64 creates a more uniform stiffness in the vertebral body 58, avoiding the significant alterations in stress distribution that would be associated with the use of bone cement alone. The more uniform stiffness in the vertebral body 58 may lower the risk for fracture in the adjacent vertebrae.

Although the use of the modulated bone augmentation material 64 has been described for use in a vertebroplasty procedure, it is understood that in alternative vertebral treatments, channels or voids may be formed in the vertebral body using probes, balloons, drills, cutting blades or other devices. In these embodiments, the mixture of gaseous bubbles and bone filling material may be used to fill the preformed voids or channels. The resulting reduced modulus material may be particularly effective in these embodiments as the otherwise unmodulated, large concentrations of bone cement accumulating in the preformed voids may give rise to significant alteration is the stress distribution.

Although the use of modulated bone augmentation material has been described primarily for vertebral body applications, it is understood that the same modulated material may be used for other procedures where reduced modulus bone cement may be desirable. For example, the modulated material may be useful for fracture repair.

In one alternative embodiment, a modulated bone augmentation material 71, including gaseous bubbles 72, may be created using the method 10 and may be used to fuse the joint section 50. The fusion of the joint 50 may be accomplished using conventional fusion techniques including transforaminal lumbar interbody fusion (TLIF), posterior lumbar interbody fusion (PLIF), or anterior lumbar interbody fusion (ALIF) procedures. Such techniques may involve the use of cages or other intervertebral spacers to maintain the height of the disc space. As a supplement or replacement for the bone graft or bone cement that would otherwise be used in a spinal fusion procedure, the modulated material 71 may be injected into the disc 60 or the disc space remaining after the removal of disc 60. The modulated material 71 may flow into crevices, voids, or prepared areas of the adjacent vertebral endplates. After hardening, the material 71 may have a modulus of elasticity similar to that of the adjacent endplates of the vertebrae 52, 54, or at least lower than unmodulated bone cement. Use of the modulated material 71 may reduce the risk of the hardened material subsiding into the endplates of the adjacent vertebrae 52, 54.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A bone augmentation system comprising:
   a mixing vessel at least partially filled with a bone filling material, the mixing vessel comprising a mixing element, wherein mixing the bone filling material with the mixing element creates a bone augmentation material including a plurality of voids;
   a pressurization source connected to the mixing vessel and adapted to prevent at least some voids in the bone augmentation material from escaping;
   a dispensing instrument comprising a dispensing reservoir adapted to receive the bone augmentation material and comprising a cannulated member adapted to deliver the bone augmentation material into a body region adjacent cancellous bone.

2. The bone augmentation system of claim 1 further comprising:
   a control mechanism operable to regulate the pressurization source.

3. The bone augmentation system of claim 1 wherein the pressurization source is an air pump.

4. The bone augmentation system of claim 1 wherein the pressurization source is a compressed gas cartridge.

5. The bone augmentation system of claim 1 wherein the mixing element comprises a rotatable mixing blade.

6. The bone augmentation system of claim 1 wherein the mixing element is an aerator.

7. The bone augmentation system of claim 1 wherein the pressurization source generates a vessel pressure greater than an atmospheric pressure within the mixing vessel.

8. The bone augmentation system of claim 1 wherein the mixing vessel is sealed.

9. The bone augmentation system of claim 1 wherein the mixing vessel is sealed and the pressurization source is a pump that pumps outside air or other gaseous substances into the mixing vessel.

10. The bone augmentation system of claim 1 wherein the mixing element comprises static mixing elements.

11. The bone augmentation system of claim 1 further comprising a pressure gauge configured to monitor pressure within the mixing vessel.

12. The bone augmentation system of claim 1 wherein the dispensing instrument comprises a plunger mechanism that is movable through the dispensing reservoir.

13. The bone augmentation system of claim 1 wherein the pressurization source is configured to generate a vessel pressure greater than an atmospheric pressure within the mixing vessel as the mixing element mixes the bone filling material to create the bone augmentation material.

14. A bone augmentation system comprising:
a bone filling material;
a mixing vessel at least partially filled with the bone filling material, the mixing vessel comprising a mixing element configured to mix the bone filling material to create a bone augmentation material including a plurality of voids;
a pressurization source connected to the mixing vessel and adapted to generate a vessel pressure greater than an atmospheric pressure within the mixing vessel to prevent at least some voids in the bone augmentation material from escaping;
a dispensing instrument comprising a dispensing reservoir adapted to receive the bone augmentation material and comprising a cannulated member adapted to deliver the bone augmentation material into a body region adjacent cancellous bone; and
a control mechanism operable to regulate the pressurization source to control pressure within the mixing vessel.

15. The bone augmentation system of claim 14 wherein the mixing vessel is sealed and the pressurization source is a pump that pumps outside air or other gaseous substances into the mixing vessel.

16. The bone augmentation system of claim 14 wherein the pressurization source is configured to generate the vessel pressure greater than the atmospheric pressure within the mixing vessel as the mixing element mixes the bone filling material to create the bone augmentation material.

17. The bone augmentation system of claim 14 wherein the bone filling material comprises a component selected from a group consisting of: polymethylmethacrylate, calcium phosphate, calcium sulfate and hydroxyapatite.

18. The bone augmentation system of claim 14 further comprising the bone augmentation material, wherein the bone augmentation material comprises plurality of voids each having a diameter between 1 and 2000 microns.

19. The bone augmentation system of claim 14 wherein the bone augmentation material comprises osteoinductive materials selected from a group consisting of: proteins from transforming growth factor (TGF) beta superfamily, bone-morphogenic proteins, BMP2 and BMP7.

20. A bone augmentation system comprising:
a bone filling material comprising a component selected from a group consisting of: polymethylmethacrylate, calcium phosphate, calcium sulfate and hydroxyapatite;
a sealed mixing vessel at least partially filled with the bone filling material, the mixing vessel comprising a mixing element configured to mix the bone filling material to create a bone augmentation material including a plurality of voids each having a diameter between 1 and 2000 microns;
a pressurization source connected to the mixing vessel and comprising a pump adapted to pump outside air or other gaseous substances into the mixing vessel to generate a vessel pressure greater than an atmospheric pressure within the mixing vessel as the mixing element mixes the bone filling material to prevent at least some voids in the bone augmentation material from escaping;
a dispensing instrument comprising a dispensing reservoir adapted to receive the bone augmentation material and comprising a cannulated member adapted to deliver the bone augmentation material into a body region adjacent cancellous bone;
a control mechanism operable to regulate the pressurization source to control pressure within the mixing vessel; and
the bone augmentation material, wherein the bone augmentation material comprises osteoinductive materials selected from a group consisting of: proteins from transforming growth factor (TGF) beta superfamily, bone-morphogenic proteins, BMP2 and BMP7.

* * * * *

UNITED STATES PATENT AND TRADEMARK OFFICE
CERTIFICATE OF CORRECTION

PATENT NO.       : 9,220,553 B2
APPLICATION NO.  : 14/474652
DATED            : December 29, 2015
INVENTOR(S)      : Trieu et al.

It is certified that error appears in the above-identified patent and that said Letters Patent is hereby corrected as shown below:

Specification

In Column 1, Lines 6-15, delete
"This application is a divisional application of U.S. patent application Ser. No. 11/622,558 filed on Jan. 12, 2007. The related applications, incorporated by reference herein, are:
U.S. Utility patent application Ser. No. 11/622,570, filed on Jan. 12, 2007 and entitled "System and Method For Forming Porous Bone Filling Material" and
U.S. Utility patent application Ser. No. 11/622,547, filed on Jan. 12, 2007 and entitled "System and Method For Forming Bone Filling Materials With Microparticles"." and insert -- The related applications, incorporated by reference herein, are:
This application is a divisional application of U.S. patent application Ser. No. 11/622,558 filed on Jan. 12, 2007.
U.S. Utility patent application Ser. No. 11/622,570, filed on Jan. 12, 2007 and entitled "System and Method For Forming Porous Bone Filling Material" and
U.S. Utility patent application Ser. No. 11/622,547, filed on Jan. 12, 2007 and entitled "System and Method For Forming Bone Filling Materials With Microparticles". --, therefor.

In Column 6, Line 4, delete "material 71," and insert -- material 64, --, therefor.

Signed and Sealed this
Fifth Day of July, 2016

Michelle K. Lee
*Director of the United States Patent and Trademark Office*